United States Patent [19]

Pálosi et al.

[11] 4,304,930
[45] Dec. 8, 1981

[54] PROCESS FOR THE PREPARATION OF 2-(3-PHENOXY-PHENYL)-PROPIONIC ACID

[75] Inventors: Endre Pálosi; Gergely Héja; Dezsö Korbonits,

[73] Assignee: Chinoin Gyógyszer- és Vegyészeti Termékek Gyára Rt, Budapest, Hungary

[21] Appl. No.: 105,988

[22] Filed: Dec. 21, 1979

[30] Foreign Application Priority Data

Dec. 29, 1978 [HU] Hungary ............................ CI 1894
Oct. 25, 1979 [HU] Hungary ............................ CI 1979

[51] Int. Cl.³ .................. C07C 51/08; C07C 59/11; C07C 121/78
[52] U.S. Cl. .................. 562/465; 260/465 F; 260/465 D; 424/304; 562/479
[58] Field of Search .................. 562/465, 479, 484

[56] References Cited

U.S. PATENT DOCUMENTS 3,853,905  12/1974  Marshall ........................ 562/465 X Primary Examiner—Dolph H. Torrence
Attorney, Agent, or Firm—Karl F. Ross

[57] ABSTRACT

2-(3-Phenoxy-phenyl)-propionic acid or its pharmaceutical treatments, are prepared by hydrolyzing and partially decarboxylating

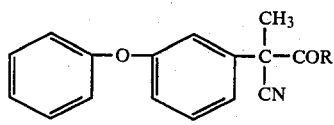

wherein $R = C_1-C_6$ alkyl or amino, the latter compounds being themselves new and, where $R = C_1-C_6$ alkyl, have antiinflammatory pharmaceutical properties.

6 Claims, No Drawings

PROCESS FOR THE PREPARATION OF 2-(3-PHENOXY-PHENYL)-PROPIONIC ACID

The present invention relates to a process for the preparation of 2-(3-phenoxy-phenyl)-propionic acid by hydrolyzing a compound of the formula

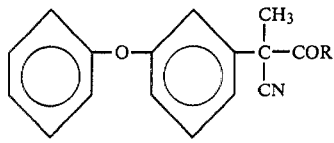

wherein R is $C_{1-6}$ alkoxy or amino, and partially decarboxylating same and converting the obtained compound—if desired—to a salt or setting it free from its salt by methods known per se.

BACKGROUND OF THE INVENTION

The anti-rheumatic activity of 2-(3-phenoxy-phenyl)-propionic acid (Fenoprofen) is known.

Several methods are disclosed for the preparation of the compound. The compound has been prepared for example by hydrolysis of 2-(phenoxy-phenyl)-3-propionitrile with sodium hydroxide in 50% aqueous ethanol for 72 hours (Swiss Patent Specification No. 527 155). The starting nitrile was prepared by methylation of m-phenoxy-acetophenone followed by reduction to α-methyl-3-phenoxy-benzylalcohol with sodium borohydride and followed by halogenation of the obtained product to α-methyl-3-phenoxy-benzyl bromide with phosphorus tribromide and reaction with sodium cyanide in anhydrous dimethyl sulfoxide (Swiss Pat. No. 527 155). According to another process α-methyl-α-(3-phenoxy-phenyl)-malonic acid is decarboxylated in a melt at 130°-160° C. The starting material was prepared by reacting α-(3-phenoxy-phenyl)-acetic acid diethyl ester with diethyl carbonate to obtain α-methyl-α-(3-phenoxyphenyl)-malonic acid diethyl ester which was hydrolyzed in aqueous alcohol by boiling it together with sodium hydroxide. The reaction mixture of the last step was purified by washing with ether in order to remove the starting ester as the hydrolysis was only partial (Swiss Pat. No. 527 155).

Further processes comprise reacting phenoxy-phenyl-magnesium bromide with the sodium salt of 2-bromo propionic acid in ether medium (Hungarian Pat. No. 168 376);

reacting 1-propynyl-3-(phenoxy)-benzene with thallium nitrate in the presence of alcohol (Hungarian Pat. No. 173 576);

oxidizing 1-isobutenyl-3-phenoxy-benzene (Spanish Pat. No. 464 352);

oxidizing phenoxy-phenyl-propionic acid aldehyde with silver oxide (German Pat. No. 2 533 397).

OBJECT OF THE INVENTION

All the enumerated processes have one common disadvantage that is using the expensive cresol as starting material. The present invention offers an economic base for the preparation of the compounds of the formula I from m-phenoxy-benzyl cyanide as starting material. The latter compound is prepared from benzyl alcohol, by halogenation thereof and by replacing halogen by cyano.

DESCRIPTION OF THE INVENTION

If as starting material a compound of the formula I is employed in which R stands for amino, a very pure 2-(3-phenoxy-phenyl)-propionic acid may be prepared by a particularly simple method.

The known processes have another disadvantage that is the necessity of an additional purification of the obtained product causing many difficulties under industrial circumstances as the boiling point of the product is very high: 168°-171° C. at 0.11 mmHg. The additional purification of 2-(3-phenoxy-phenyl)-propionic acid is necessary in each case of the known processes, because the formed intermediate products are also difficult to purify due to their high boiling point.

At the same time in pharmaceutical technology the purity of the starting materials is a basic requirement.

According to the present invention 2-(3-phenoxy-phenyl)-propionic acid may be prepared from a compound of the formula I, wherein R is amino, i.e. from 2-cyano-2-(3-phenoxy-phenyl)-propionic acid amide and thus the additional purification of the product may be avoided. 2-Cyano-2-(3-phenoxy-phenyl)-propionic acid amide is a solid substance which may, if desired, be purified by simple crystallization and thus rather impure starting materials may also be employed and thus the process becomes economic.

Compounds of the formula I used as starting material in the process of the invention are new compounds and are also the subject of the present invention.

The invention also provides a process for the preparation of the compounds of the formula I.

Compounds of the formula I are prepared by reacting m-phenoxy-benzyl cyanide with $C_{1-6}$ dialkyl carbonate in the presence of a basic catalyst, by methylating the thus obtained new 2-cyano-2-(3-phenoxy-phenyl)-acetic acid $C_{1-6}$ alkyl ester and reacting optionally the obtained compound of the formula I, wherein R is $C_{1-6}$ alkoxy, with a compound suitable for the introduction of an amino group into the molecule, preferably with ammonia.

According to a preferable embodiment of the present invention m-phenoxy-benzyl cyanide is heated with diethyl carbonate in an anhydrous organic solvent, preferably in a lower alcohol, advantageously in ethanol in the presence of equimolar amount of alkali alkoxide, preferably sodium ethoxide. It has been found surprisingly that the condensation may be carried out with better results than by the generally used method known from the state of art of similar reactions, which comprises carrying out the synthesis by elimination of ethanol by heating with an excess of diethyl carbonate and removing the formed alcohol by a continuous azeotropic distillation (Org. Synth. Coll. Vol. IV. p. 461).

According to the present invention the reaction is carried out in a homogeneous solution; thus the reaction time is shorter and 2-cyano-2-(3-phenoxy-phenyl)-acetic acid $C_{1-6}$ alkyl ester is formed with a higher yield and purity. Preferably 1 to 2.5 moles of diethyl carbonate are used for 1 mole m-phenoxy-benzyl cyanide. The thus prepared 2-cyano-2-(3phenoxy-phenyl)-acetic acid $C_{1-6}$ alkyl ester is separated, if desired, or preferably treated with a methylating agent without isolation. As the methylating agent dimethyl sulphate or methyl iodide are used. The methylating agent is used in an excess of 5 to 100%. If as starting material 2-cyano-2-(3-phenoxy-phenyl)-acetic acid $C_{1-6}$ alkyl ester is employed, then the starting material is dissolved in a solution of sodium ethoxide, preferably in an equimolar amount in anhydrous ethanol and heated with the methylating agent.

The obtained compound of the formula I, wherein R is $C_{1-6}$ alkoxy, is isolated, if desired, or preferably used for the preparation of 2-cyano-2-(3-phenoxy-phenyl)-propionic acid amide without isolation or preferably by reacting it with ammonia in solution.

As a solvent organic solvents, such as alcohols, particularly methanol or ethanol, may be used. The reaction of 2-cyano-(3-phenoxy-phenyl)-propionic acid alkyl ester takes place in the solvent containing ammonia. The reaction may be carried out by heating or without heating. The reaction may be carried out at a temperature range of from 0° to 150° C., preferably 20° to 100° C. The compounds of the formula I containing $NH_2$ as R, are obtained substantially with theoretical yield, and if desired, may be simply isolated as the product crystallizes upon cooling in the form of colorless crystals.

If the product contains impurities, it may be simply purified by recrystallization from aqueous alcoholic solution.

The optionally isolated and purified compound of the formula I or a solution containing same are preferably hydrolyzed in water or in an aqueous organic solvent mixture in the presence of a base or an acid. One may employ mineral acids, such as sulphuric acid or hydrochloric acid, inorganic bases, such as alkali and alkali earth metal-hydroxides or organic acids or organic bases. The reaction is preferably accelerated by heating. The product is obtained with nearly theoretical yield. According to a particularly preferable embodiment of the process hydrolysis and partial decarboxylation of the compound of the formula I is carried out by heating in an aqueous $C_{1-4}$ alcoholic solution in the presence of an alkali hydroxide. 2-(3-Phenoxy-phenyl)-propionic acid is then obtained by distillation of the excess of the alcohol and by acidifying. The salt of the formed 2-(3-phenoxy-phenyl)-propionic acid may be obtained by methods known per se. Alkali metal, alkali earth metal and amine salts are preferably prepared. The calcium salt of the compound is most preferred. If in the course of the reaction a salt of 2-(3-phenoxy-phenyl)-propionic acid is obtained, then the free acid can be set free from its salt.

The new compounds of the formula I and the $C_{1-6}$ alkyl ester of the new 2-cyano-2-(3-phenoxy-phenyl)-acetic acid possess anti-inflammatory activity.

SPECIFIC EXAMPLES

The further details of the invention are illustrated by the following Examples which serve merely for illustration and not for limitation.

EXAMPLE 1

A mixture of 189 g. of m-phenoxy-benzaldehyde and 1 liter of 1 molar isopropyl alcoholic aluminum isopropoxide solution is distilled under stirring through a column as long as acetone may be detected in the cut by using 2,4-dinitro-phenyl-hydrazine. It takes about 2 to 3 hours. The rate of distillation is controlled so that within this time about 200 ml of distillate can be collected. The excess of isopropyl alcohol is then distilled off in vacuo. To the residue 500 g. of ice and 550 ml. of 20% aqueous hydrochloric acid solution are added. The separated oil is shaken out with 2×1 liter of benzene and the benzene solution is dried above sodium sulphate. When the benzene is distilled off 195 g. (97.4%) of m-phenoxy-benzyl alcohol is obtained, the purity of which is more than 95% (determined by gas chromatography).

EXAMPLE 2

To a solution of 200 g. of m-phenoxy-benzyl alcohol in 1 liter of dry chloroform 2 ml. of pyridine are added and a solution of 142.8 g. thionyl-chloride in 150 ml. of chloroform is added dropwise under cooling with ice water. When the addition is completed the cooling is terminated and the solution is allowed to warm up to room temperature under stirring and the temperature is maintained under stirring until the vigorous gas evolution ceases. The mixture is then boiling under stirring until the gas evolution ceases completely. The solution is then poured into 2 liters of cold water, the chloroform layer is separated and the aqueous layer is shaken out in 400 ml. of chloroform. The combined chloroform solutions are washed once with water and dried above sodium sulphate. The drying agent is filtered off and chloroform is distilled off; thus 210 g. (96%) of m-phenoxy-benzyl chloride are obtained, which can be distilled at 128° to 130° C. at a pressure of 0.3 mmHg. Substantially no forerun and residue are obtained.

EXAMPLE 3

To a solution of 218 g. m-phenoxy-benzyl chloride in 850 ml. of 96% ethyl alcohol a solution of 57.8 g. of sodium cyanide in 100 ml. of water is added at once. The reaction mixture is boiled under stirring until the starting material cannot be detected anymore by thin layer chromatography. When the reaction is completed the reaction mixture is poured into 1 liter of water and the separating oil is extracted with 3×500 ml. of benzene. The combined benzene solutions are washed with 1 liter of water and dried above sodium sulphate. Sodium sulphate is filtered off and benzene is distilled off. 190 g. (91%) of m-phenoxy-benzyl cyanide are obtained (purity more than 90%, determined by gas chromatography). Boiling point 138° C./0.2 mmHg.

EXAMPLE 4

To a solution of 23 g. sodium in 500 ml. of anhydrous alcohol 209 g. of m-phenoxy-benzyl cyanide and 260 g. of diethyl carbonate are added. The reaction mixture is boiled under stirring for 2.5 hours, whereafter it is poured into 3.5 liter of water and acidified with 58 ml. of acetic acid. The separating oil is shaken out with 2×500 ml. of chloroform. The combined chloroform solutions are dried above sodium sulphate and evaporated. The oily residue consisting of 2-(3-phenoxy-phenyl)-2-cyano-acetic acid ethyl ester is distilled in vacuo, boiling point: 187°–192° C./0.2 mmHg; $n_D{}^{27}$: 1.5568.

Similarly, but substituting 183 g. of dimethyl carbonate for diethyl carbonate (3-phenoxy-phenyl)-cyano acetic acid is obtained (74%), b.p.: 178°–182° C./0.2 mmHg; $n_D{}^{25}$: 1.5015.

EXAMPLE 5

To a solution of 23 g. of sodium in 500 ml. of anhydrous alcohol 209 g. of m-phenoxy-benzyl cyanide and 260 g. of diethyl carbonate are added. The reaction mixture is boiled under stirring for three hours and after cooling 126 g. of dimethyl sulphate are added dropwise in portions and the mixture is boiled under stirring for further 5 hours. The main part of the alcohol is distilled off and the residue is admixed with 3 liter of water. The 2-(3-phenoxy-phenyl)-2-cyano-propionic acid ethyl ester separating in the form of oil is extracted with 3×500 ml. of benzene. The benzene solution is evaporated in vacuo after drying above sodium sulphate. On the residue 250 ml. of methanol containing 15% ammonia is poured and the mixture is maintained for 3 hours at a temperature of 90° to 100° C. in a bomb tube. The reaction mixture is processed as given in Example 6 and thus 220 g. (92.5%) of 2-(3-phenoxy-phenyl)-2-cyano-propionic acid amide are obtained; m.p.: 128°–130° C.

EXAMPLE 6

A solution of 90 g. of 2-(3-phenoxy-phenyl)-2-cyano-propionic acid ethyl ester in 90 ml. of methanol containing 15% ammonia is maintained in a bomb tube at 90°–100° C. for 3 hours. At this time the starting ester can no longer be detected by thin layer chromatography. The solution is cooled and the precipitating crystals are filtered by suction and dried. 69 g. of (85%) 2-(3-phenoxy-phenyl)-2-cyano-propionic acid amide are obtained; m.p.: 128°–130° C. By evaporating the mother liquor further 11 g. of the product are obtained; m.p.: 123°–125° C.

Total yield: 98.5%.

After recrystallization from 50% aqueous alcohol the product melts at 134°–135° C.

Analysis: $C_{16}H_{14}N_2O_2$; calculated: C%=72.16; H%=5.26; N%=10.52; found: C%=71.88; H%=5.40; N%=10.43.

NMR—1.9 ppm, methyl, 3 H; in $CHCl_3$—6.15 ppm, $NH_2$ 2 H.

6.7–7.5 ppm aromatic protons—9 H.

According to the above procedure, but using 86 g. of 2-(3-phenoxy-phenyl)-2-cyano propionic acid methyl ester, 2-(3-phenoxy-phenyl)-2-cyano-propionic acid amide is obtained; m.p.: 123°–125° C.

EXAMPLE 7

The same procedure is followed as in Example 6 but instead of being heated the reaction mixture is allowed to stand in a closed vessel for 48 hours at room temperature. From 90 g. of 2-(3-phenoxy-phenyl)-2-cyano-propionic acid ethyl ester 78 g. (96%) 2-(3-phenoxy-phenyl)-2-cyano-propionic acid amide are obtained.

EXAMPLE 8

A mixture of 106.4 g. of 2-(3-phenoxy-phenyl)-2-cyano-propionic acid amide, 200 ml. of 40% aqueous sodium hydroxide and 400 ml. of alcohol is boiled under stirring for 20 hours. The alcohol is then distilled off and the residue is diluted with 200 ml. of water. The aqueous solution is acidified to pH=1 by adding concentrated hydrochloric acid. The separating oil is extracted with 3×500 ml. of benzene. The benzene solution is evaporated after drying above sodium sulphate. Thus 96 g. (98.5%) 2-(3-phenoxy-phenyl)-propionic acid are obtained; the product is suitable for the preparation of salts without further purification.

EXAMPLE 9

90 g. of the crude 2-(3-phenoxy-phenyl)-propionic acid prepared according to Example 8 are dissolved in 740 ml. of 0.5 n sodium hydroxide solution. The pH of the solution is 7 to 8. The solution is treated with decolorizing charcoal, 370 ml. of alcohol are added and the mixture is heated to 70° C. At this temperature 100 ml. of 2 molar aqueous calcium chloride solution is added dropwise under stirring within 30 minutes. The solution containing the crystalline precipitate is allowed to cool to room temperature under stirring. The mixture is then allowed to stand for a few hours in ice water, whereafter the white crystals are filtered by suction, washed with 2×100 ml. of 30% aqueous alcohol and air dried.

Thus 90 g. (86.5%) calcium salt of 2-(3-phenoxy-phenyl)-propionic acid are obtained; m.p.: 115°–120° C.

EXAMPLE 10

To a solution of 8.85 g. of sodium in 175 ml. of anhydrous alcohol 108.5 g. of 2-(3-phenoxy-phenyl)-2-cyano-acetic acid ethyl ester and in portions 48.7 g. of dimethyl sulphate are added. The reaction mixture is stirred at room temperature until the exothermic reaction is completed whereafter it is boiled for 5 hours. The reaction mixture is cooled and poured into 2 liters of water. The separated oil is extracted with 3×250 ml. of chloroform. The combined chloroform solutions are washed with water and dried above sodium sulphate. The chloroform solution is evaporated and the residue consisting of 2-(3-phenoxy-phenyl)-2-cyano-propionic acid ethyl ester is distilled in vacuo. B.p.: 155°–157° C./0.05 mmHg; $n_D^{25}$: 1.5490.

When using 103 g. of m-phenoxy-phenyl-cyano acetic acid methyl ester as the starting material 2-(3-phenoxy-phenyl)-2-cyano-propionic acid methyl ester is obtained, yield: 82.5%; b.p.: 174° C./0.1 mmHg; $n_D^{26}$: 1.5520.

EXAMPLE 11

To a solution of 118 g. of 2-(3-phenoxy-phenyl)-2-cyano-propionic acid ethyl ester in 226 ml. of ethyl alcohol 226 ml. of 10 n sodium hydroxide solution is added and the reaction mixture is boiled under stirring until the gas evolution ceases. The alcohol is distilled off and the residue is dissolved in water. The pH of the solution is adjusted to 1 by adding concentrated hydrochloric acid. The separating oil is extracted with 2×100 ml. of benzene. The combined benzene solution is evaporated after drying above sodium sulphate and the residual 2-(3-phenoxy-phenyl)-propionic acid is distilled in vacuo. B.p.: 168°–171° C./0.1 mmHg.

When using 113 g. of 2-(3-phenoxy-phenyl)-2-cyano-propionic acid methyl ester as the starting material 2-(3-phenoxy-phenyl)-propionic acid of the same physical properties is obtained.

EXAMPLE 12

One may proceed as described in Example 2, but dimethyl sulphate is replaced by 88 g. of methyl iodide. The obtained product is identical with the product prepared according to Example 10.

EXAMPLE 13

To a solution of 23 g. of sodium in 500 ml. of anhydrous alcohol 209 g. of m-phenoxy-benzyl cyanide and 145 g. of diethyl carbonate are added. The reaction mixture is boiled under stirring and after cooling 126 mg. of dimethyl sulphate are added dropwise in portions and the mixture is boiled under stirring for a further 5 hours. To the reaction mixture 500 ml. of 10 n sodium hydroxide solution is added and the mixture is boiled under stirring until the gas evolution ceases. When the reaction is completed the alcohol is distilled off. The residue is dissolved in water. The pH of the solution is adjusted to 1 by adding concentrated hydrochloric acid. The separated oil is taken up in 500 ml. of benzene. The benzene solution is evaporated after drying above sodium sulphate and the residual 2-(3-phenoxy-phenyl)-propionic acid is distilled off. B.p.: 168°–171° C./0.1 mmHg. Yield: 206 g. (85%).

What we claim is:

1. A process for the preparation of 2-(3-phenoxy-phenyl-propionic acid or a pharmaceutically effective salt thereof which comprises hydrolyzing and partially decarboxylating 2-cyano-2-(3-phenoxy-phenyl)-propionic acid amide in water or in an aqueous organic solvent mixture in the presence of a base or an acid.

2. The process defined in claim 1 wherein the aqueous organic solvent is a $C_1$ to $C_4$ alcoholic solution and the base is an alkali hydroxide and wherein the 2-(3-phenoxy-phenyl)-propionic acid or a pharmaceutically acceptable salt thereof is obtained by distilling off the excess of the $C_1$ to $C_4$ alcoholic solution and by acidifying.

3. The process defined in claim 1 wherein the 2-cyano-2-(3-phenoxy-phenyl)-propionic acid amide is prepared by the following steps:
    (a) reacting m-phenoxy-benzyl-cyanide with a $C_1$ to $C_6$ dialkyl carbonate in the presence of a basic catalyst to obtain a $C_1$ to $C_6$ alkyl-ester of 2-cyano-2-(3-phenoxy-phenyl)-acetic acid;
    (b) methylating the $C_1$ to $C_6$ alkyl-ester of 2-cyano-2-(3-phenoxy-phenyl)-acetic acid to form a $C_1$ to $C_6$ alkyl-ester of 2-cyano-2-(3-phenoxy-phenyl)-propionic acid; and
    (c) reacting the $C_1$ to $C_6$ alkyl-ester of 2-cyano-2-(3-phenoxy-phenyl)-propionic acid with a compound suitable to introduce an amino group into the molecule to form the 2-cyano-2-(3-phenoxy-phenyl)-propionic acid amide.

4. The process defined in claim 3 further comprising the following steps:
    (d) crystalizing the 2-cyano-2-(3-phenoxy-phenyl)-propionic acid amide to purify same.

5. The process defined in claim 1 wherein the 2-cyano-2-(3-phenoxy-phenyl)-propionic acid amide is prepared by the following steps:
    (a) methylating a $C_1$ to $C_6$ alkyl-ester of 2-cyano-2-(3-phenoxy-phenyl)-acetic acid to form a $C_1$ to $C_6$ alkyl-ester of 2-cyano-2-(3-phenoxy-phenyl)-propionic acid; and
    (b) reacting the $C_1$ to $C_6$ alkyl-ester of 2-cyano-2-(3-phenoxy-phenyl)-propionic acid with a compound suitable to introduce an amino group into the molecule to form the 2-cyano-2-(3-phenoxy-phenyl)-propionic acid amide.

6. The process defined in claim 5 further comprising the following step:
    (c) crystalizing the 2-cyano-2-(3-phenoxy-phenyl)-propionic acid amide to purify same.

* * * * *

UNITED STATES PATENT AND TRADEMARK OFFICE
CERTIFICATE OF CORRECTION

PATENT NO. : 4,304,930

DATED : December 8, 1981

INVENTOR(S) : Endre Pálosi et al

It is certified that error appears in the above-identified patent and that said Letters Patent is hereby corrected as shown below:

On the title page, left column, item (75) inventors should read after "korbonits," insert -- Pál Kiss, Csaba Gönczi, Judit Cser, Ida Szvoboda, Gábor Szabó, Tamás Kállay, László Ledniczky, Mária Szomor, all of Budapest, Hungary --

Signed and Sealed this

Twenty-third Day of November 1982

[SEAL]

Attest:

Attesting Officer

GERALD J. MOSSINGHOFF

Commissioner of Patents and Trademarks